United States Patent [19]
Pond

[11] 4,017,508
[45] Apr. 12, 1977

[54] BENZOXAZOLE ULTRAVIOLET STABILIZERS AND THEIR USE IN ORGANIC COMPOSITIONS

[75] Inventor: David Martin Pond, Kingsport, Tenn.

[73] Assignee: Eastman Kodak Company, Rochester, N.Y.

[22] Filed: July 1, 1974

[21] Appl. No.: 484,849

[52] U.S. Cl. .................... 260/307 D; 260/332.2 A; 260/332.2 C; 260/346.2 R; 260/347.4; 260/472; 260/45.8 R; 260/45.8 RW; 260/45.8 A; 260/45.8 SN; 260/45.8 NZ; 260/45.8 NE; 260/45.8 NT; 260/45.85; 260/240 D; 260/240.1; 260/302 D; 260/302 H; 260/304 R; 260/307 DA; 260/307 G; 260/308 R; 260/308 B; 260/309; 260/309.2; 260/310 C; 260/326.13 R; 260/326.14 R; 260/330.5
[51] Int. Cl.$^2$ ....................................... C07D 263/56
[58] Field of Search ................................ 260/307 D

[56] References Cited
UNITED STATES PATENTS 3,864,354  2/1975  Irick et al. ..................... 260/307 D

*Primary Examiner*—Raymond V. Rush
*Attorney, Agent, or Firm*—Clyde L. Tootle; Daniel B. Reece, III

[57] ABSTRACT

The invention relates to certain benzoxazole bichromophoric compounds which have been found to be effective ultraviolet stabilizers. The invention also relates to ultraviolet degradable organic compositions containing a stabilizing amount of a certain benzoxazole bichromophoric compound to prevent such degradation. These stabilizers are effective in the presence of other additives commonly employed in polymeric compositions including, for example, pigments, colorants, fillers, reinforcing agents and the like. These ultraviolet stabilizers may also be incorporated into the organic compositions such as polymers by adding to the polymer melt or dissolved in the polymer dope, coated on the exterior of the shaped or molded article, film or extruded fiber.

15 Claims, No Drawings

BENZOXAZOLE ULTRAVIOLET STABILIZERS AND THEIR USE IN ORGANIC COMPOSITIONS

This invention relates to ultraviolet stabilizers, more particularly, the invention relates to stabilization of organic compositions against deterioration resulting from the exposure to light with a new class of diesters of resorcinol compounds.

The degradative effects of ultraviolet light on various organic compositions is well known in the art. The photodeterioration or degradation is of particular concern with organic photo-degradable compositions which are exposed to ultraviolet light, such as sunlight, for long periods of time. One group of such photodegradable organic compositions is polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photodegradation problem of polymeric compositions. As a result of this effort, there have been discovered many additives and stabilizers which improve the stability of polymeric compositions.

Moreover, various organic compounds exhibit the power to absorb electromagnetic radiations within the band of 2900 to 4000 A. and when incorporated in various plastic materials such as transparent sheets, the resultant sheet acts as a filter for all of the radiation passing through and will transmit only such radiations as are not absorbed by the sheet and/or the absorbing agent. It is thus possible to screen out undesirable radiations and minimize the resulting transparent sheet as a filter in many technical and commercial applications such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photodegradation. Therefore, to provide a more effective and efficient ultraviolet stabilizer for organic compositions susceptible to such degradation would be an advance in the state of the art.

It is, therefore, an object of the present invention to provide more effective and efficient ultraviolet light stabilizer compositions.

Another object of the present invention is to provide useful compositions characterized by improved resistance to ultraviolet degradation and deterioration.

It is still another object of the present invention to provide compositions containing diesters of aromatic diols which are resistant to ultraviolet degradation.

A further object of this invention to provide processes for improving the resistance of organic materials to deterioration and degradation by actinic radiation and especially ultraviolet radiation.

A still further object of this invention to provide compositions and processes for improving the resistance of organic materials to deterioration and degradation by actinic radiations including short wave length visible radiations.

Other objects will appear as the description proceeds.

In accordance with the present invention aryl diesters of aromatic compounds are provided which can be used as ultraviolet stabilizers. These compositions, according to the present invention, have the following structure

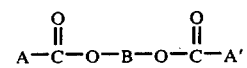

wherein A is a benzoid or heterocyclic group having the following structure:

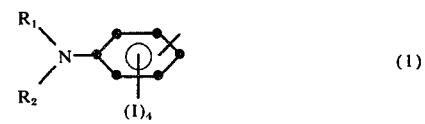

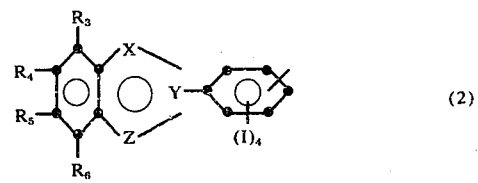

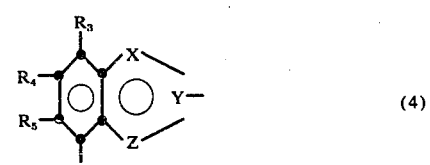

wherein

X and Y are a carbon atom or a nitrogen atom;

Z is an oxygen atom, a sulfur atom, a nitrogen atom, a nitrogen atom containing a hydrogen atom or a substituted or unsubstituted lower alkyl group containing 1 to 12 carbon atoms;

$R_1$ and $R_2$ are either substituted and unsubstituted alkyl groups containing 1 to 20 carbon atoms or substituted and unsubstituted aryl groups containing 6, 12 or 18 carbon atoms; $R_3$, $R_4$, $R_5$, $R_6$ and $R_7$ are hydrogen, lower alkyl, substituted lower alkyl, cycloalkyl, substituted cycloalkyl, aryl, halogen, substituted aryl, lower alkylaryl, aryl-substituted-aryl, alkoxy, carboxy, nitrile, and the substituents $R_3$ and $R_4$, $R_4$ and $R_5$, $R_5$ and $R_6$, $R_6$ and $R_7$, combined with the carbon atoms to which they are attached, are joined alkylene groups completing a carboxylic ring which can be substituted with any of the substituents listed above for $R_3$, $R_4$, $R_5$, $R_6$ and $R_7$.

I is a substituent listed above for $R_3$, $R_4$, $R_5$ and $R_6$ and is present on all positions of the benzenoid ring, except the carbon atom attached to the Y substituent and the carbon atom attached to the carboxyl group connecting the heterocyclic aromatic A group with the aromatic B group. The carbonyl connecting group is attached to the benzoin ring in either the meta or para position from the carbon atom connected to the Y substituent. The I substituents can all be one of the substituents listed above or different listed substituents.

The group C is a moiety consisting of vinyl, lower alkyloxy, oxy-lower-alkyl and oxy;

The group D is a moiety having the structure

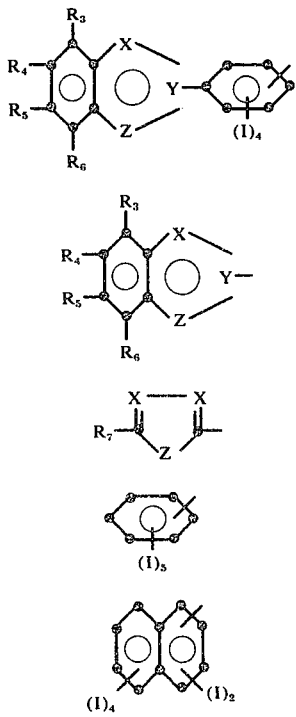

wherein

X and Y are a carbon atom or a nitrogen atom;

Z is an oxygen atom, a sulfur atom, a nitrogen atom, or a nitrogen atom containing a hydrogen atom or substituted or unsubstituted lower alkyl group having 1 to 12 carbon atoms;

$R_3$, $R_4$, $R_5$, $R_6$ and $R_7$ are hydrogen, lower alkyl, substituted lower alkyl, cycloalkyl, substituted cycloalkyl, aryl, substituted aryl, lower alkylaryl, aryl-substituted-aryl, chloro, bromo, alkoxy, substituted amino, cyano, carboxy and the substituents $R_3$ and $R_4$, $R_4$ and $R_5$, and $R_5$ and $R_6$, combined with the carbon atoms to which they are attached, are joined alkylene groups completing a carbocyclic ring, which ring can also be substituted with one or more of the substituents listed above for $R_3$, $R_4$, $R_5$ and $R_6$.

I is a substituent listed above for $R_3$, $R_4$, $R_5$ and $R_6$ and is present on all positions of the benzenoid ring, except the carbon atom attached to the Y substituent and the carbon atom attached to the carboxyl group connecting the heterocyclic aromatic A group with the aromatic B group. The carbonyl connecting group is attached to the benzoin ring in either the meta or para position from the carbon atom connected to the Y substituent. The I substituents can all be one of the substituents listed above or different listed substituents.

As hereinbefore used, the term "lower alkyl" denotes branched or unbranched, substituted or unsubstituted alkyl groups containing 1 to 12 carbon atoms. The "alk" of the alkoxy or carboalkoxy denotes an alkyl group of 1 to 20 carbon atoms. The substituted alkyl, aryl, or cycloalkyl group can be substituted with any of the substituents listed hereinbefore for $R_3$.

B is an aryl group having the formula

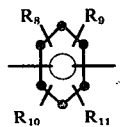

wherein the carboxys attached ortho, meta, or para, at least one of $R_8$, $R_9$, $R_{10}$, $R_{11}$ is hydrogen in the ortho position to the carboxy linking group and the other substituents $R_8$–$R_{11}$ are hydrogen, lower alkyl, substituted lower alkyl, cycloalkyl, lower alkylaryl, aryl-substituted-aryl, alkoxy, carboxy, nitrile, chloro, bromo, and the substituents $R_8$–$R_{11}$, combined with the carbon atoms to which they are attached, are joined alkylidene groups completing a carbocyclic ring which can be substituted with any of the substituents listed above for $R_8$–$R_{11}$.

A' is an aryl group such as phenyl, substituted phenyl, naphyl or substituted naphyl or the same benzoid or heterocyclic group as A. Substituents on the A' substituted phenyl and naphyl groups can be the same as I described hereinabove.

Suitable A groups having the structure

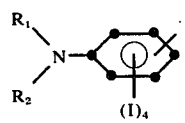

are, for example, dialkylanilines such as dimethylaniline, diethylaniline, bis-($\beta$-chloroethyl)aniline, bis-($\beta$-hydroxyethyl)aniline, di-n-propylaniline, and the like; arylalkylanilines such as methylphenylaniline, ethylphenylaniline, and the like; and diaryl anilines such as diphenylaniline di-(p-alkoxyphenyl)aniline, di-(p-halophenyl)aniline, di-(p-cyanophenyl)aniline, and the like.

Suitable A groups having the structure

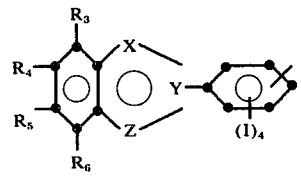

are, for example, substituted and unsubstituted benzoxazoles, benzotriazoles, benzothiazoles, and benzamidazoles.

Examples of such suitable benzoxazole moieties are those having the formula

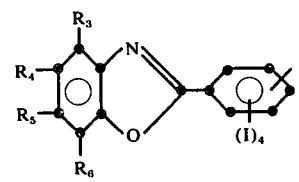

such as 4-(5,6-dimethyl-2-benzoxazolyl)phenyl, 4-(2-benzoxazolyl)-2-chlorophenyl, and 3-(5-chloro-2-benzoxazolyl)phenyl.

Examples of suitable benzotriazole moieties are those having the formula

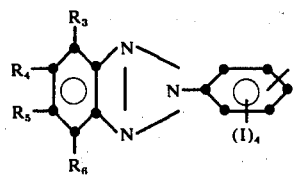

such as 4-(5-chloro-2H-benzotriazol-2-yl)phenyl, 4-(2H-benzotriazol-2-yl)phenyl, and 4-(5-methoxy-2H-benzotriazol-2-yl)phenyl.

Examples of suitable benzothiazole moieties are those having the formula

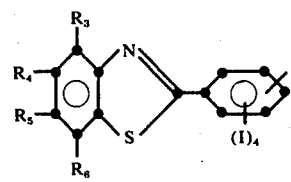

such as 4-(5,6-dimethyl-2-benzothiazolyl)phenyl, 4-(2-benzothiazolyl)-2-chlorophenyl, and 3-(5-chloro-2-benzothiazolyl)phenyl.

Examples of suitable benzimidazole moieties are those having the formula

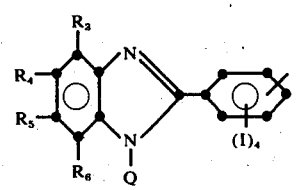

wherein Q is hydrogen or a substituted or unsubstituted lower alkyl group containing 1 to 12 carbon atoms, such as 4-(5,6-dimethyl-2-benzimidazolyl)-phenyl, 4-(2-benzimidazolyl)-2-chlorophenyl, 3-(5-chloro-2-benzimidazolyl)-phenyl, 4-(1-methyl-2-benzimidazolyl)phenyl, 4-(1-ethyl-5-chloro-2-benzimidazolyl)phenyl, and N-ethyl 4-(2-benzimidazolyl)-phenyl.

Examples of suitable indole moieties are those having the formula

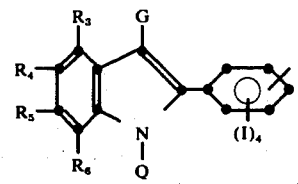

wherein G is the same as $R_3$ and Q is hydrogen or a substituted or unsubstituted lower alkyl containing 1 to 12 carbon atoms, such as 3-(1-ethyl-3-cyano-2-indolyl)phenyl, 3-(5-chloro-2-indolyl)phenyl, 3-(1-methyl-2-indolyl)phenyl, 3-(3-methyl-2-indolyl)phenyl, 3-(3-chloro-2-indolyl)phenyl, 3-(5-acetamido-2-indolyl)phenyl, 3-(2-indolyl)phenyl, 4-(1-ethyl-2-indolyl)phenyl, 4-(3-cyano-2-indolyl)phenyl, 4-(5-methoxy-2-indolyl)phenyl, 4-(1-methyl-2-indolyl)phenyl, 4-(3-methyl-5-phenyl-2-indolyl)phenyl, 4-(3,5-dichloro-2-indolyl)phenyl, 4-(2-indolyl)phenyl, 4-chloro-2-indolylphenyl, and 4-methoxy-2-indolylphenyl.

Suitable A groups having the structure

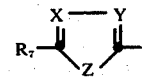

are oxadiazole, benzopyrole, triazine, thiadiazole, substituted and unsubstituted 2-oxadiazolyl, 2-thiazolyl, 2-triazolyl, 2-oxazolyl, and 2-imidazolyl and the like.

Examples of suitable oxadizaole moieties are those having the formula

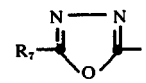

such as 5-phenyl-1,3,4-oxadiazol-2-yl, 5-methylsulfonyl-1,3,4-oxadiazol-2-yl, 5-(2,4-dichlorophenyl)-1,3,4-oxadiazol-2-yl, 5-(4-chlorophenyl)-1,3,4-oxadizaol-2-yl, 5-methyl-1,3,4-oxadiazol-2-yl, 5-(4-phenyl)phenyl-1,3,4-oxadiazol-2-yl, 5-cyano-1,3,4-oxadiazol-2-yl, 5-(4-cyanophenyl)-1,3,4-oxadiazol-2-yl, and 5-(4-methoxyphenyl)-1,3,4-oxadiazol-2-yl, and the like.

Examples of suitable 2-thiadiazolyl moieties are those having the formula:

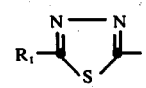

such as 5-phenyl-1,3,4-thiadiazol-2-yl, 5-(4-chlorophenyl)-1,3,4-thiadiazol-2-yl, 5-methylsulfonyl-1,3,4-thiadiazol-2-yl, 5-ethoxy-1,3,4-thiadiazol-2-yl, 5-phenyl-1,3,4-thiadiazol-2-yl, 5-(4-phenyl)phenyl-1,3,4-thiadiazol-2-yl, 5-cyclohexyl-1,3,4-thiadiazol-2-yl, 5-(3-methoxyphenyl)-1,3,4-thiadiazol-2-yl, and 5-cyano-1,3,4-thiadiazol-2-yl, and the like.

Examples of suitable 2-triazolyl moieties are those having the formula:

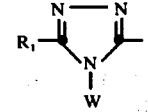

wherein W is hydrogen or a substituted or unsubstituted lower alkyl group containing 1 to 12 carbon atoms, such as 5-phenyl-1,3,4-triazol-2-yl, 5-(4-cyanophenyl)-1,3,4-triazol-2-yl, 5-cyano-1,3,4-triazol-2-yl, 4-(4-methoxyphenyl)-1,3,4-triazol-2-yl, 1-(n-butyl)-5-(2,4-dichlorophenyl)-1,3,4-triazol-2-yl, 1,3,4-triazol-2-yl, 5-phenyl-1,3,4-triazol-2-yl, 5-methylsulfonyl-1,3,4-triazol-2-yl, 1-methyl-5-phenyl-1,3,4-triazol-2-yl, and the like.

Examples of suitable 2-oxazolyl moieties are those having the formula:

wherein J is the same as R₁, such as 5-phenyl-2-oxazolyl, 4,5-diphenyl-2-oxazolyl, 4,5-dimethyl-2-oxazolyl, 4-chloro-5-cyano-2-oxazolyl, 4-phenyl-5-cyano-2-oxazolyl, 5-methylsulfonyl-2-oxazolyl, 5-cyclohexyl-2-oxazolyl, 4,5-dichloro-2-oxazolyl, 5-ethoxy-2-oxazolyl, and the like.

Examples of suitable 2-thiazolyls are thiazolyls having the formula:

wherein J is the same as R₁, such as 4-phenyl-5-chloro-2-thiazolyl, 4,5-dichloro-2-thiazolyl, 4-chloro-5-cyano-2-thiazolyl, 4-ethoxy-5-phenyl-2-thiazolyl, 4,5-dimethyl-2-thiazolyl, 4,5-dicyano-2-thiazolyl, 5-phenyl-2-thiazolyl, and the like.

Examples of suitable 2-imidazolyl moieties are those having the formula:

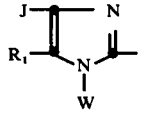

wherein J is the same as R₁ and W is hydrogen or a substituted or unsubstituted lower alkyl having 1 to 12 carbon atoms, such as 1-methyl-4,5-diphenyl-2-imidazolyl, 4-chloro-5-cyano-2-imidazolyl, 5-phenyl-2-imidazolyl, 1-ethyl-5-phenyl-2-imidazolyl, 4,5-diphenyl-2-imidazolyl, 1-benzyl-4-phenyl-5-cyano-2-imidazolyl, 1-methyl-4-cyano-2-imidazolyl, 4-methoxy-5-phenyl-2-imidazolyl-4,5-dichloro-1-benzyl-2-imidazolyl, and the like.

Suitable A groups having the formula

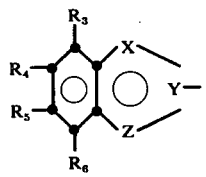

are, for example, substituted and unsubstituted 2-benzoxazolyl, 2-benzothiazolyl, 2-benzimidazolyl, benzotriazolyl and 2-imidolyl.

Examples of suitable 2-benzoxazolyl moieties are those having the formula

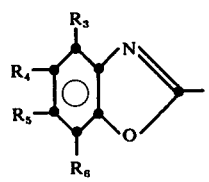

such as 5,6-dimethyl-2-benzoxazolyl, 2-benzoxazolyl, 5-chloro-2-benzoxazolyl, 5,6-dichloro-2-benzoxazolyl, 4,5-diethyl-2-benzoxazolyl, 5-cyano-2-benzoxazolyl, 5-methoxy-6-methyl-2-benzoxazolyl, 4-chloro-5-phenyl-2-oxazolyl.

Examples of suitable 2-benzothiazolyl moieties are those having the formula

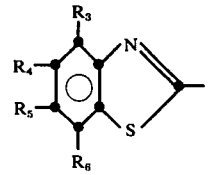

such as 2-benzothiazolyl, 5,6-dimethyl-2-benzothiazolyl, 5,6-dichloro-2-benzothiazolyl, 5-chloro-2-benzothiazolyl, 5-methoxy-2-benzothiazolyl, 6-methylsulfonyl-2-benzothiazolyl, 6-cyano-2-benzothiazolyl, 6-methylthio-2-benzothiazolyl, and 6-methyl-2-benzothiazolyl.

Examples of suitable 2-benzimidazolyl moieties are those having the formula

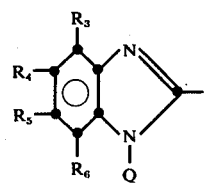

wherein Q is hydrogen or a substituted or unsubstituted lower alkyl containing 1 to 12 carbon atoms, such as 2-benzimidazolyl, 1-methyl-2-benzimidazolyl, 1,5,6-trimethyl-2-benzimidazolyl, 6-cyano-1-ethyl-2-benzimidazolyl, 6-chloro-2-benzimidazolyl, 5-methoxy-1-benzyl-2-benzimidazolyl, 6-methylsulfonyl-2-benzimidazolyl, 4-methoxy-1-methyl-2-benzimidazolyl, and the like.

Examples of suitable indole moieties are those having the formula

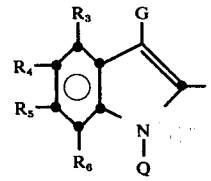

wherein G is the same as R₃ and Q is hydrogen or a substituted or unsubstituted lower alkyl containing 1 to 12 carbon atoms. Such suitable indole moieties are, for example, 1-ethyl-3-cyano-2-indolyl, 5-chloro-2-indolyl, 1-methyl-2-indolyl, 3-methyl-2-indolyl, 3-chloro-2-indolyl, 5-acetamido-2-indolyl, 1-benzyl-2-indolyl, 1-ethyl-2-indolyl, 3-cyano-2-indolyl, 5-methoxy-2-indolyl, 1-methyl-2-indolyl, 3-methyl-5-phenyl-2-indolyl, 3,5-dichloro-2-indolyl and 2-indolyl.

Examples of suitable triazine moieties are those having the formula

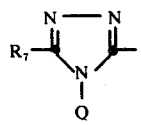

where Q is hydrogen or lower alkyl containing 1 to 12 carbon atoms, such as 1H-5-phenyl-1,3,4-triazol-2-yl, 1H-5-methylsulfonyl-1,3,4-triazol-2-yl, 1-methyl-5-phenyl-1,3,4-triazol-2-yl, and 1-ethyl-5-(4-chlorophenyl)-1,3,4-2-yl.

Examples of suitable thiadiazole moieties are those having the formula

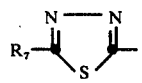

such as 5-phenyl-1,3,4-thiadiazol-2-yl, 5-(4-chlorophenyl)-1,3,4-thiadiazol-2-yl and 5-methylsulfonyl-1,3,4-thiadiazol-2-yl.

Suitable A' groups can be the same as A or phenyl or substituted phenyls, naphyl or substituted naphyl and the like.

Suitable B groups are phenyl moieties having the formula

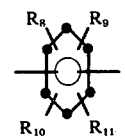

are for example, catechol, resorcinol, p-hydroquinone, 4-methylcatechol, 4-methoxycatechol, 5-methylresorcinol, 5-methoxyresorcinol, 2,5-dimethylresorcinol, tolylhydroquinone, 2,5-dimethylhydroquinone, t-butylhydroquinone and 5-t-butylresorcinol.

The bichromophoric compounds can be prepared by reacting acid chlorides with dihydroxybenzenes.

For example, one group of bichromics ultraviolet stabilizer according to the present invention is prepared as follows:

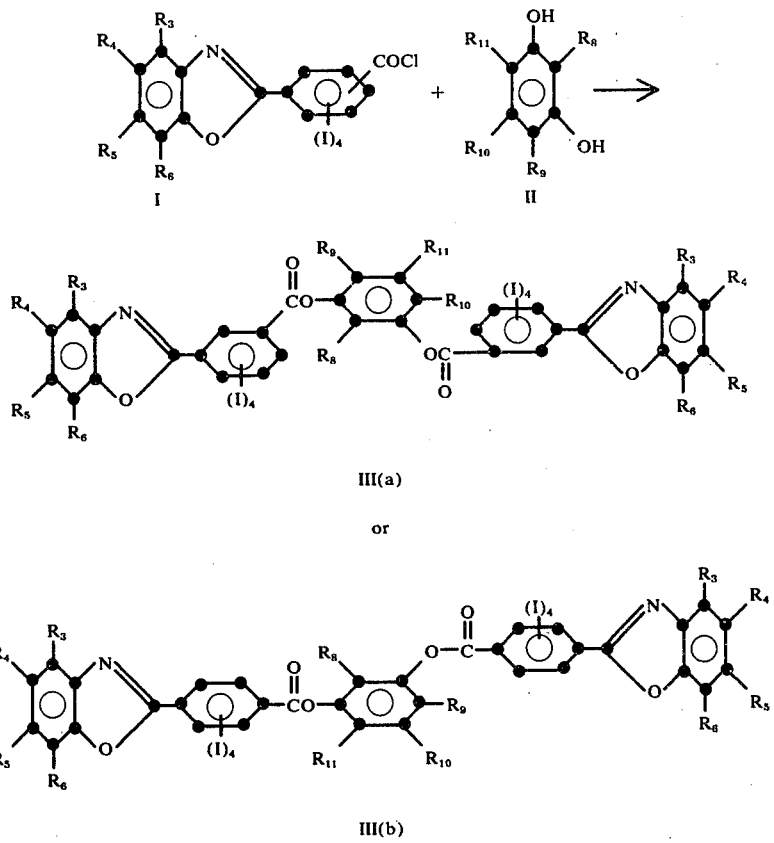

wherein $R_3$ through $R_{11}$ and I and II are defined hereinabove.

It is necessary that at least one of $R_8$, $R_9$ or $R_{11}$ be hydrogen so that, on exposure to ultraviolet light, the aryl ester of the heterocyclic aromatic acid is capable by a "photo-Fries" rearrangement of forming a phenol group in that position formerly joined through an oxygen atom to the carbonyl linking group, as for example

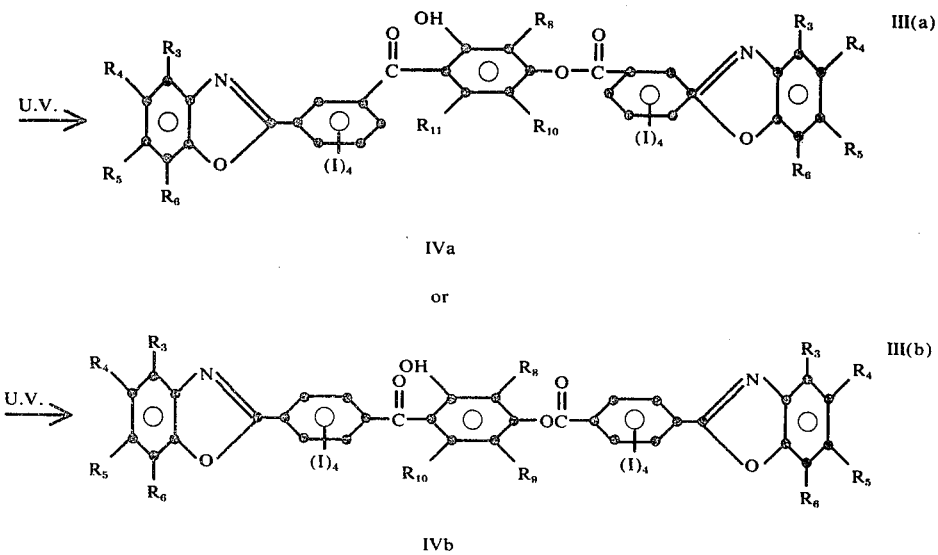

The acid chlorides (I) were prepared by reaction of the corresponding acids [see *Zh. Obshch. Khim.*, 38, 1001-5 (1968); *Chem. Abstr.*, 69, 96568 (1968)] with freshly distilled thionyl chloride [see *J. Chem. Soc.*, 101, 2476 (1912)]. The aromatic diols such as resorcinol, catechol or p-hydroquinone were obtained from commercial sources, or were prepared by standard methods; a necessary requirement is that one of the positions adjacent the hydroxyl moiety on the benzene ring of the diol be unsubstituted.

The heterocyclic phenylene dibenzoate compositions can be added to organic compositions which are susceptible to ultraviolet degradation. Such compositions include, for example, polymeric compositions such as polyester fiber and moldable compositions, such as polyethylene terephthalate, polytetramethylene terephthalate and the like; polyolefins such as, for example, high, medium and low density polyethylene, polypropylene, polybutene and the like; polyamides such as N-methoxymethyl polyhexamethylene adipamide and the like; polycarbonates; polyvinyl chloride and copolymers; cellulose esters; acrylic/butadiene/styrene plastic; polyacrylics such as methyl methacrylate; polystyrene; gelatin; vinylidene chloride copolymers such as vinylidene chloride/vinyl acetate copolymers; ethylene/vinyl acetate copolymers; cellulose esters such as methyl cellulose; polyvinyl esters such as polyvinyl acetate; polyethylene oxides; polyvinyl acetals; polyformaldehydes; and polyurethanes. Such compositions also include natural and synthetic rubbers, such as polybutadiene, and unsaturated organic compositions such as oils and the like, as well as compositions containing such organic compositions.

The heterocyclic phenylene dibenzoate compositions as effective ultraviolet stabilizers or screening agents are generally used in an amount of from 0.01 to 10%, by weight, based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10%, by weight, provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from about 0.1 to about 3%, by weight. For example, an amount of 2% by weight of the stabilizer effectively stabilizes cellulose acetate butyrate plastic compositions.

The ultraviolet stabilized organic compositions containing the stabilizers of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These novel heterocyclic phenylene dibenzoate ultraviolet stabilizers may be incorporated into organic compositions by melt-blending or may be added onto the surface of an organic plastic material prior to being molded into a suitable object, or added to the surface of the molded object. These materials can also be added to coatings and the like which can be applied to the surface of a molded object.

This invention will be further illustrated by the following examples although it will be understood that these examples are included merely for purposes of illustration and are not intended to limit the scope of the invention.

EXAMPLE 1 m-Phenylene 4-(2-benzoxazolyl)dibenzoate can be prepared by the following procedure:

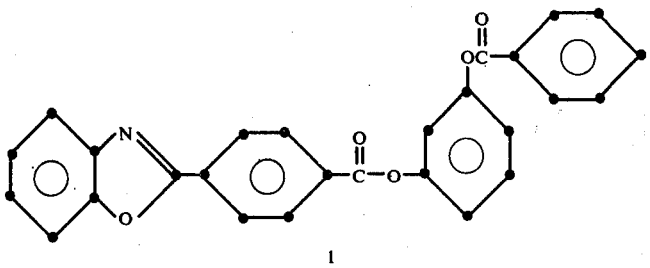

1

A solution containing 14.4 g (0.05 mole) of 4-(2-benzoxazolyl)benzoyl chloride, 10.7 g. (0.05 mole) of resorcinol monobenzoate, and 5 ml. of pyridine in 250 ml. of toluene is refluxed for 15 hours. The solution is filtered hot and, upon concentration of the filtrate, 17.09 g. (78%) of m-phenylene 4-(2-benzoxazolyl)-dibenzoate (1) is filtered as a crystalline solid having a melting point of 174°–175° C.: UV (CH$_3$CN) λmax. 318 nm. (ε35,600).

Other phenylene benzoxazolyldibenzoates can be prepared by substituting other benzoxazolylbenzoyl chlorides, such as 4-(5,6-dimethyl-2-benzoxazolyl)-benzoyl chloride, 4-(2-benzoxazolyl)-2-chlorobenzoyl chloride, 3-(5-chloro-2-benzoxazolyl)benzoyl chloride, 4-(5,6-dichloro-2-benzoxazolyl)benzoyl chloride, (4-(5,6-diethyl-2-benzoxazolyl)benzoyl chloride, 4-(5-cyano-2-benzoxazolyl)benzoyl chloride, 4-(5-methoxy-6-methyl-2-benzoxazolyl)benzoyl chloride, for 4-(2-benzoxazolyl)benzoyl chloride.

EXAMPLE 2 m-Phenylene bis(p-2-benzoxazolylbenzoate) can be prepared by the following procedure:

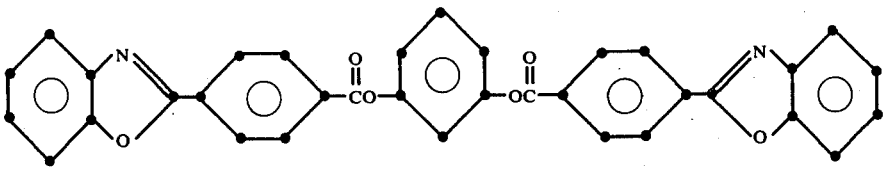

2

A solution containing 2.75 g. (0.025 mole) of resorcinol and 2.0 g. (0.050 mole) of sodium hydroxide in 75 ml. of water is added dropwise to a chloroform solution (200 ml.) of 4-(2-benzoxazolyl)benzoyl chloride (12.85 g., 0.050 mole). The resulting solution is refluxed for 4 hours. An off-white solid which appears between the layers is filtered and air-dried and amounts to 10.60 g. (77%) of m-phenylene bis(p-2-benzoxazolylbenzoate) (2) having a melting point of 273°–274° C.: UV (CH$_3$CN) λmax. 319 nm. (ε73,000).

Other phenylene benzoxazolyldibenzoates can be prepared by substituting other benzoazolylbenzoyl chlorides, such as 4-(5,6-dimethyl-2-benzoxazolyl)-benzoyl chloride, 4-(2-benzoxazolyl)-2-chlorobenzoyl chloride, 3-(5-chloro-2-benzoxazolyl)benzoyl chloride, 4-(5,6-dichloro-2-benzoxazolyl)benzoyl chloride 4-(5,6-diethyl-2-benzoxazolyl)benzoyl chloride, 4-(5-cyano-2-benzoxazolyl)benzoyl chloride, 4-(5-methoxy-6-methyl-2-benzoxazolyl)benzoyl chloride, for 4-(2-benzoxazolyl)benzoyl chloride.

Also, other phenylene benzoxazolyldibenzoates can be prepared by substituting other aromatic diols, such as 5-methylresorcinol, 5-methoxyresorcinol, 5-chlororesorcinol, 2-methyl-p-hydroquinone, 2-methoxy-p-hydroquinone, 2,5-dimethyl-p-hydroquinone, 2,5-dimethoxy-p-hydroquinone, 4-methylcatechol, 4-methoxycatechol, 4-chlorocatechol, 4,5-dimethylcatechol, 4,5-dimethoxycatechol, 4,5-dichlorocatechol, for resorcinol.

EXAMPLE 3 o-Phenylene bis(p-2-benzoxazolylbenzoate) can be prepared by the following procedure:

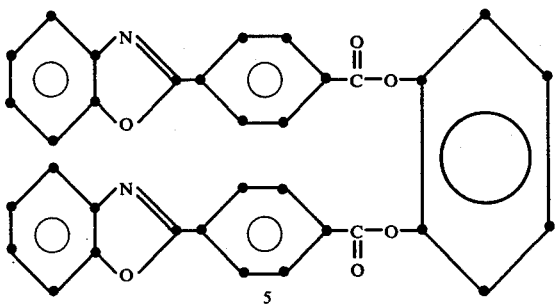
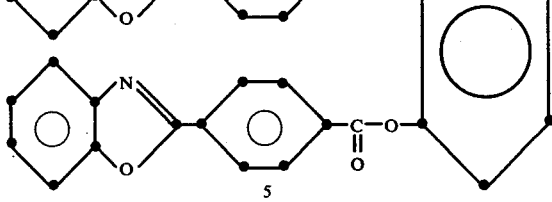
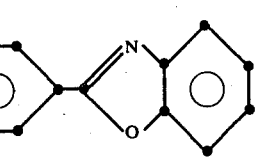

5

A solution containing 1.65 g. (0.015 mole) of catechol and 1.20 g. (0.03 mole) of sodium hydroxide in 20 ml. of water was added to a chloroform solution (60 ml.) of 4-[2-benzoxazolyl]benzoyl chloride (7.70 g., 0.03 mole) and refluxed for 5 hours. An off-white solid which appears between the layers was filtered, washed with ether and air dried and amounts to 7.01 g. (84%) of o-phenylene bis(p-2-benzoxazolyl)benzoate (5) (mp 221°–225°) UV (CH$_2$Cl$_2$) max 308 nm. (ε50,000).

EXAMPLE 4 m-Phenylene 4-[2-(5,6-dimethyl-2-benzoxazolyl)-vinyl]dibenzoate can be prepared by the following procedure:

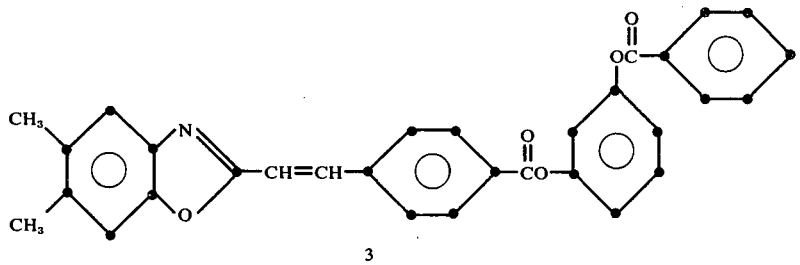

3

A solution containing 3.12 g. (0.01 mole) of 4-[2-(5,6-dimethyl-2-benzoxazolyl)vinyl]benzoyl chloride, 2.15 g. (0.01 mole) of resorcinol monobenzoate, and 10 ml. of pyridine in 150 ml. of toluene is refluxed for 5 hours. The solution is filtered hot and, upon concentration of the filtrate, 3.53 g. (72%) of m-phenylene 4-[2-(5,6-dimethyl-2-benzoxazolyl)vinyl]dibenzoate (3) is obtained as a light yellow solid having a melting point of 198°–199° C.: UV (CH₃CN) εmax. 358 nm. (ε40,500); ε325 = 26,000.

EXAMPLE 5 m-Phenylene 4,4'-bis[2-(5,6-dimethyl-2-benzoxazolyl)vinyl]dibenzoate can be prepared by the following procedure:

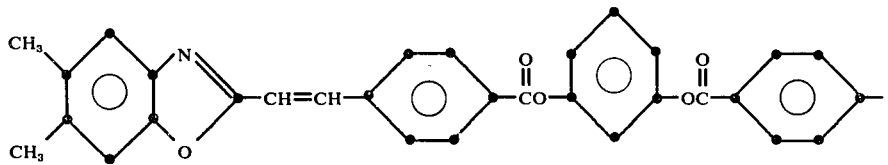

4

A solution containing 1.10 g. (0.01 mole) of resorcinol and 0.83 g. (0.02 mole) of sodium hydroxide in 50 ml. of water is added dropwise to a chloroform solution (125 ml.) of 4-[2-(5,6-dimethyl-2-benzoxazolyl)vinyl]benzoyl chloride (6.23 g., 0.02 mole) and refluxed for 18 hours. The organic layer is separated, washed with water, dried, and concentrated to give 4.56 g. (40%) of m-phenylene 4,4'-bis-[2-(5,6-dimethyl-2-benzoxazolyl)vinyl]dibenzoate (4) having a melting point of 225°–227° C.: UV (CH₃CN) εmax. 357 nm. (70,000) ε325 = 44,000.

EXAMPLE 6

The ultraviolet stabilization provided by the heterocyclic phenyl benzoates of the present invention is shown in poly(tetramethylene terephthalate) in the following table.

Flat bars of polyester containing these stabilizers are prepared and exposed to a 280–700 nm. mercury lamp source until a flatwise impact strength of less than 6 is obtained (initial values are all greater than 15). The results are summarized in Table 1. Stabilizers 1 to 4 are:

1. m-phenylene 4-(2-benzoxazolyl)dibenzoate
2. m-phenylene bis(p-2-benzoxazolylbenzoate)
3. m-phenylene 4-[2-(5,6-dimethyl-2-benzoxazolyl)vinyl]dibenzoate
4. m-phenylene 4,4'-bis[2-(5,6-dimethyl-2-benzoxazolyl)vinyl]dibenzoate.

Table 1

| Effect of Stabilizers on Time-To-Loss of Impact Strength of Polytetramethylene Terephthalate | |
|---|---|
| Stabilizer (concentration) | Time-To-Loss of Impact Strength (hr.) |
| None | <500 (300) |
| Tinuvin P (0.5) | <1000 |
| 1 (0.5) | 1000 |
| 2 (0.5) | >1700 |
| 3 (0.5) | >1000 |
| 4 (0.5) | >1000 |

These diesters of aromatic acid compositions find particular utility as ultraviolet stabilizers in organic compositions requiring ultraviolet stability. Such compositions include polymeric compositions such as, for example, polyester fiber and molding compositions; poly-α-olefins; polyamides; acrylics; cellulose esters and the like; as well as molded or shaped articles, film and coatings formed from such materials, and the like. Such compositions also include natural and synthetic rubbers, such as natural rubber, as well as organic materials such as oils, fats, and unsaturated organic materials, and materials having such materials contained therein such as paints, varnishes, cosmetics and the like.

The invention has been described in detail with particular reference to preferred embodiments thereof, but it will be understood that variations and modifications can be effected within the spirit and scope of the invention.

We claim:
1. A composition of matter having the formula:

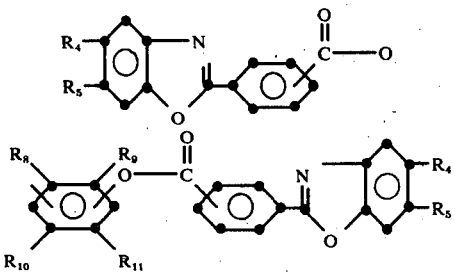

wherein $R_4$ is hydrogen, lower alkyl, or nitrile; $R_5$ is hydrogen or lower alkyl; and at least one $R_8$, $R_9$, $R_{10}$ and $R_{11}$ is hydrogen, and the remainder are hydrogen, lower alkyl, alkoxy containing 1 to 20 carbon atoms, halogen, or nitrile or carboalkoxy containing 1 to 20 carbon atoms.

2. A composition of matter having the formula:

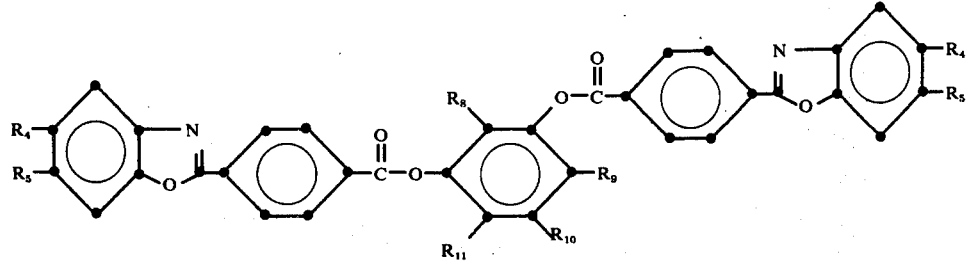

wherein $R_4$ is hydrogen, lower alkyl, or nitrile; $R_5$ is hydrogen or lower alkyl; and at least one $R_8$, $R_9$, and $R_{11}$ is hydrogen, and the remaining $R_8$, $R_9$, $R_{10}$ and $R_{11}$ are hydrogen, lower alkyl, alkoxy containing 1 to 20 carbon atoms, halogen or nitrile.

3. A composition of matter having the formula:

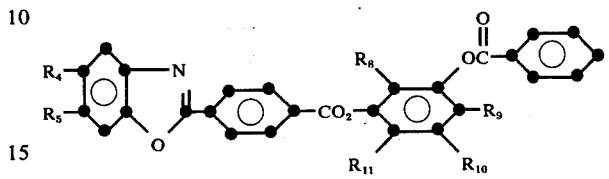

wherein $R_4$ is hydrogen, phenyl lower alkyl wherein said alkyl contains not more than three carbon atoms or lower alkyl; $R_5$ is hydrogen or lower alkyl; and at least one $R_8$, $R_9$, and $R_{11}$ are hydrogen, and the remaining $R_8$, $R_9$, $R_{10}$ and $R_{11}$ are hydrogen, lower alkyl, alkoxy containing 1 to 20 carbon atoms, halogen, nitrile, or carboxy.

4. A composition of matter having the formula:

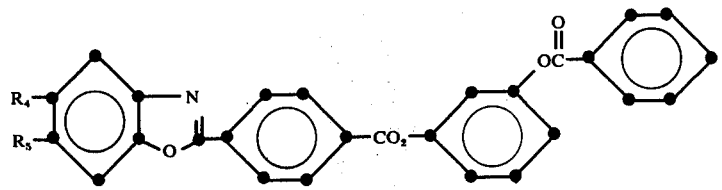

wherein $R_4$ is hydrogen, lower alkyl, or nitrile; $R_5$ is hydrogen or lower alkyl; and at least $R_8$, $R_9$, and $R_{11}$ is hydrogen and the remaining $R_8$, $R_9$, $R_{10}$ and $R_{11}$ are hydrogen, lower alkyl, alkoxy containing 1 to 20 carbon atoms, halogen or nitrile or carboxy.

5. A composition of matter having the formula:

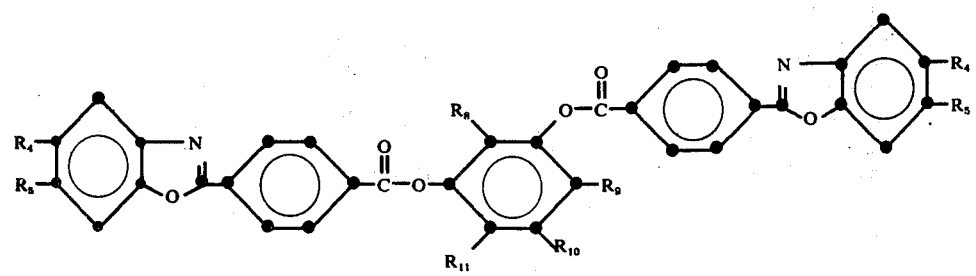

wherein $R_4$ is hydrogen or lower alkyl and $R_5$ is hydrogen or lower alkyl.

6. A composition of matter according to claim 5 having the formula:

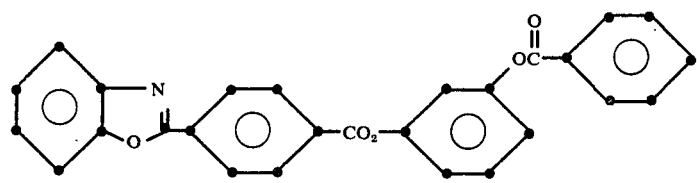
7. A composition of matter having the formula:
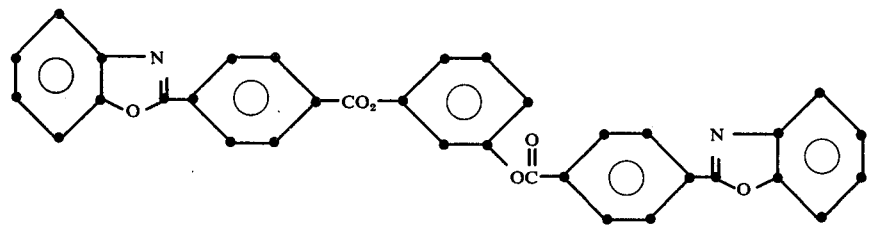
8. A composition of matter having the formula:
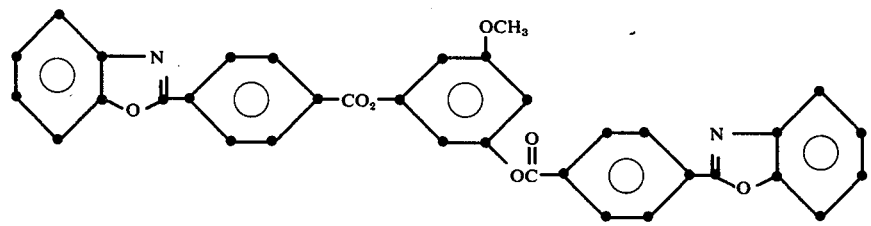
9. A composition of matter having the formula:
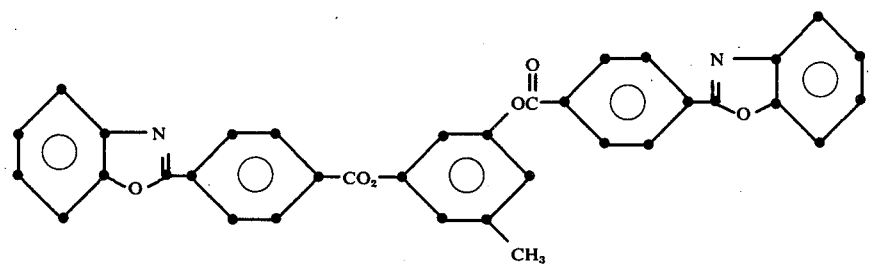
10. A composition of matter having the formula:
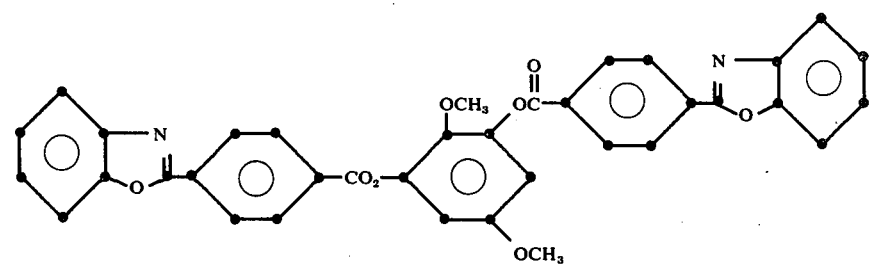
11. A composition of matter having the formula:

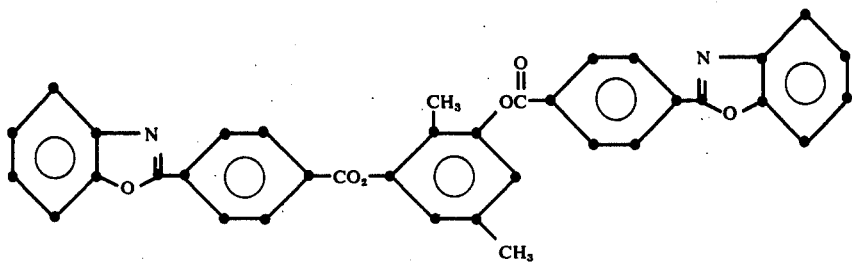
12. A composition of matter having the formula:
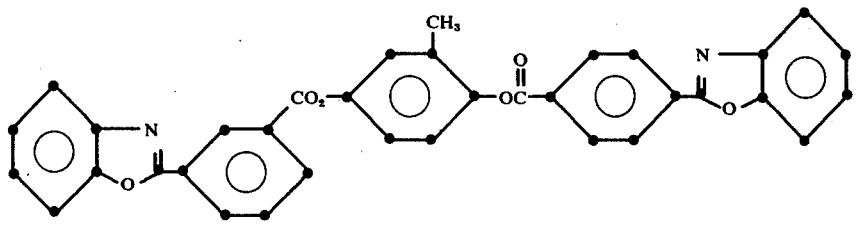
13. A composition of matter having the formula:
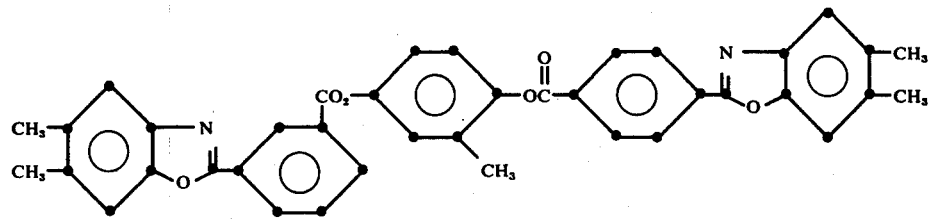
14. A composition of matter having the formula:
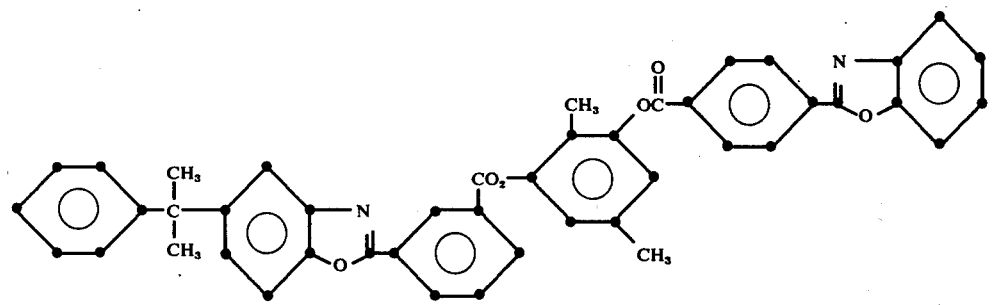
15. A composition of matter having the formula:
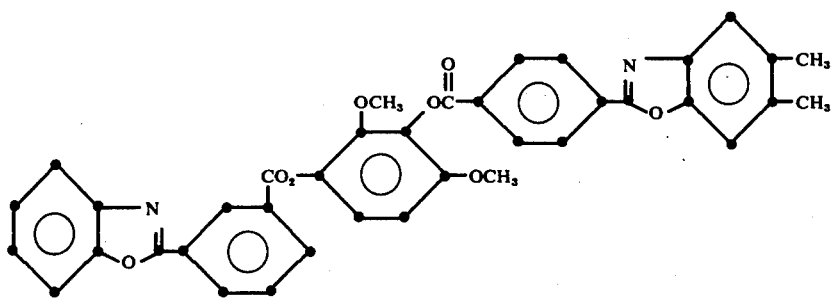
* * * * *

UNITED STATES PATENT OFFICE
CERTIFICATE OF CORRECTION

Patent No. 4,017,508                    Dated April 12, 1977

Inventor(s) David M. Pond

It is certified that error appears in the above-identified patent and that said Letters Patent are hereby corrected as shown below:

Column 17, Claim 3, the structural formula should read

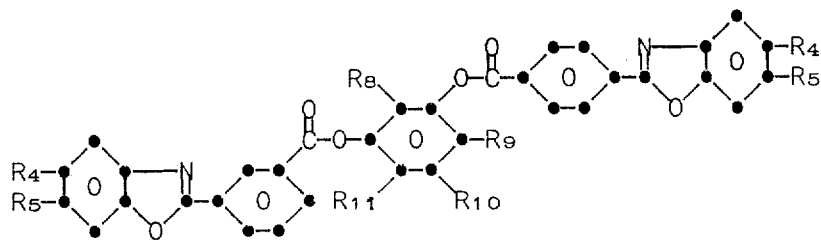

Column 18, line 19, after the word "least" insert ---one---.

Signed and Sealed this

Thirteenth Day of September 1977

[SEAL]

Attest:

RUTH C. MASON
Attesting Officer

LUTRELLE F. PARKER
Acting Commissioner of Patents and Trademarks